United States Patent
Ho et al.

(10) Patent No.: US 10,958,962 B2
(45) Date of Patent: Mar. 23, 2021

(54) VIDEO RECOMMENDING SYSTEM AND VIDEO RECOMMENDING METHOD

(71) Applicant: AmTRAN Technology Co., Ltd., New Taipei (TW)

(72) Inventors: Che-Chia Ho, New Taipei (TW); Yu-Hsaing Lin, New Taipei (TW)

(73) Assignee: AmTRAN Technology Co., Ltd., New Taipei (TW)

( * ) Notice: Subject to any disclaimer, the term of this patent is extended or adjusted under 35 U.S.C. 154(b) by 0 days.

(21) Appl. No.: 16/734,430

(22) Filed: Jan. 6, 2020

(65) Prior Publication Data
US 2020/0228859 A1   Jul. 16, 2020

(30) Foreign Application Priority Data
Jan. 14, 2019   (TW) ................................ 108101408

(51) Int. Cl.
| H04N 21/422 | (2011.01) |
| H04N 21/25  | (2011.01) |
| A61B 5/16   | (2006.01) |
| G06T 19/00  | (2011.01) |
| G02B 27/01  | (2006.01) |

(52) U.S. Cl.
CPC ....... *H04N 21/42201* (2013.01); *A61B 5/165* (2013.01); *G06T 19/006* (2013.01); *H04N 21/251* (2013.01); *G02B 27/017* (2013.01); *G06F 2203/011* (2013.01)

(58) Field of Classification Search
CPC .......... H04N 21/42201; H04N 21/251; H04N 21/44218; H04N 21/4826; H04N 21/4753; A61B 5/165; A61B 2503/12; A61B 5/04842; G06T 19/006; G02B 27/017; G06F 2203/011
See application file for complete search history.

(56) References Cited

U.S. PATENT DOCUMENTS

| 8,392,250 B2 | 3/2013 | Pradeep et al. |
| 9,983,670 B2 | 5/2018 | Coleman et al. |
| 10,009,644 B2 | 6/2018 | Aimone et al. |
| 2015/0033258 A1* | 1/2015 | Klappert ............ H04N 21/4316 725/38 |
| 2017/0007165 A1* | 1/2017 | Jain ...................... A61B 5/7445 |
| 2019/0364084 A1* | 11/2019 | Huang ................ H04L 65/4084 |

FOREIGN PATENT DOCUMENTS

| CN | 107341333 A | 11/2017 |
| TW | 201424688 A | 7/2014 |

* cited by examiner

*Primary Examiner* — Mulugeta Mengesha
*Assistant Examiner* — Alazar Tilahun
(74) *Attorney, Agent, or Firm* — CKC & Partners Co., LLC

(57) ABSTRACT

A video recommending system includes a virtual reality device and a server. The virtual reality device includes a brainwave sensor and a processor. The brainwave sensor is configured to acquire a first brainwave data. The processor is coupled to the brainwave sensor, and is configured to receive the first brainwave data. The server is coupled to the virtual reality device. The server is configured to generate a recommending list according to a first emotion data corresponding to the first brainwave data, and to transmit the recommending list to the virtual reality device, wherein the recommending list includes a plurality of video lists for the virtual reality device to play at least one video of the video lists.

10 Claims, 3 Drawing Sheets

VIDEO RECOMMENDING SYSTEM AND VIDEO RECOMMENDING METHOD

CROSS-REFERENCE TO RELATED APPLICATION

This application claims priority to and the benefit of Taiwan Application Serial Number 108101408, filed on Jan. 14, 2019, the entire content of which is incorporated herein by reference as if fully set forth below in its entirety and for all applicable purposes.

BACKGROUND

Field of Disclosure

The disclosure generally relates to video system and method, and more particularly, to video recommending system and method.

Description of Related Art

In the development of consumer devices, the entertainment products for consumers trends to diversity. Generally, when the consumers decide to purchase or participate in a product, they may often deliberate on information which is provided by provides. However, each consumer's habit, preference, life experience, and the like, are different. Although the suggestions or information from the providers are considered, the consumers may have unpleasant experience which is resulted from the inconsistency between the personal experience and the providers' suggestions or information. Accordingly, how to reduce the discrepancy between the consumers' actual experience and the expected experience is an urgent problem to be solved.

SUMMARY

The following presents a simplified summary of one or more aspects of the present disclosure, in order to provide a basic understanding of such aspects. This summary is not an extensive overview of all contemplated features of the disclosure, and is intended neither to identify key or critical elements of all aspects of the disclosure nor to delineate the scope of any or all aspects of the disclosure. Its sole purpose is to present some concepts of one or more aspects of the disclosure in a simplified form as a prelude to the more detailed description that is presented later.

One aspect directed towards a video recommending system. The video recommending system includes a virtual reality device and a server. The virtual reality device includes a brainwave sensor and a processor. The brainwave sensor is configured to acquire a first brainwave data. The processor is coupled to the brainwave sensor, and is configured to receive the first brainwave data. The server is coupled to the virtual reality device. The server is configured to generate a recommending list according to a first emotion data corresponding to the first brainwave data, and to transmit the recommending list to the virtual reality device. The recommending list includes a plurality of video lists for the virtual reality device to play at least one video of the video lists.

One aspect directed towards a video recommending method is disclosed, which includes steps of acquiring a first brainwave data; analyzing the first brainwave data to generate a first emotion data; generating a recommending list according to the first emotion data; transmitting the recommending list to a virtual reality device, wherein the recommending list comprises a plurality of video lists; and playing, by the virtual reality device, at least one video of the video lists.

It is to be understood that both the foregoing general description and the following detailed description are by examples, and are intended to provide further explanation of the disclosure as claimed.

DETAILED DESCRIPTION

Figure 1:
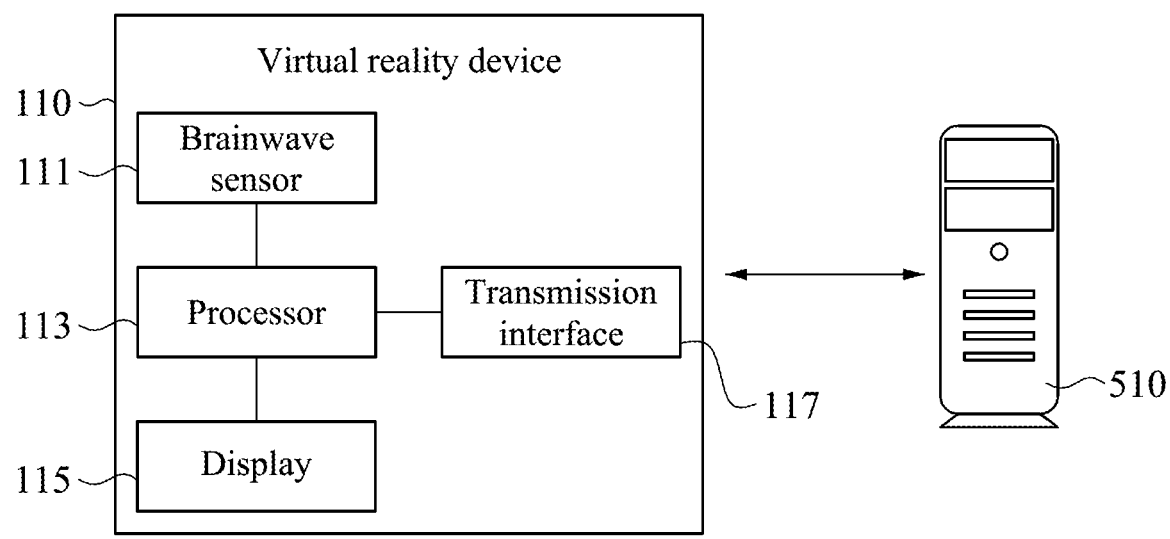
FIG. 1 is a block diagram illustrating an example of a video recommending system in accordance with some aspects of the present disclosure.

Reference will now be made in detail to the present embodiments of the disclosure, examples of which are illustrated in the accompanying drawings. Wherever possible, the same reference numbers are used in the drawings and the description to refer to the same or like parts.

Reference is made to FIG. 1, which is a block diagram illustrating an example of a video recommending system 100 in accordance with some aspects of the present disclosure. As shown in FIG. 1, the video recommending system 100 includes a virtual reality device 110 and a server 510. In some embodiments, the virtual reality device 110 plays video for user who wears the virtual reality device 110 to watch video, meanwhile a brainwave data is recorded while he/she is watching video. Furthermore, the virtual reality device 110 analyzes the brainwave data to obtain an emotion data, and the emotion data (or its classification) is transmitted to the server 510. In some other embodiments, the virtual reality device 110 also transmits the brainwave data of the user who is watching video to the server 510, such that the server 510 analyzes the brainwave data to obtain the user's emotion data or classification when watching the video. Therefore, the server 510 might build the relationship between the classification of the video genre and the classification of the emotion data of the user according to the emotion data of the user watching video. Then, a much more suitable video genre can be recommended to the user (for example, according to current emotional status or reaction of the user).

The virtual reality device 110 includes a brainwave sensor 111, a processor 113, a display 115, and a transmission interface 117. The brainwave sensor 111, the display 115, and the transmission interface 117 are coupled to the processor 113. In some embodiments, when the user wears virtual reality device 110 on his/her head, the user's brain produces an electrical wave or an electromagnetic wave while the user is watching video, i.e., a brainwave signal. The brainwave sensor 111 receives the user's brainwave signal to generate a brainwave data. The brainwave data can be, but is not limited to, P300 wave, Lambda ($\lambda$) wave, Gamma ($\gamma$) wave, Beta ($\beta$) wave, Alpha ($\alpha$) wave, Theta ($\theta$) wave, Delta ($\delta$) wave, and so on.

In some embodiments, the genre of the brain data and signal strength corresponding to each genre of the brain data is obtained by analyzing the frequency or electric potential difference of the brainwave data via the processor 113. For example, the processor 113 analyzes that the brainwave data is provided with frequency range from 20 to 100 Hz and then determines that the brainwave is the Gamma (γ) wave. Taking the signal strength is set from 0 to 100 as an example, when the signal strength is estimated to be 60, the signal strength of Gamma (γ) wave is determined to be medium strength. In some other embodiments, the processor 113 analyzes the frequency of the brainwave data is provided with the frequency range from 15 to 28 Hz, and the processor 113 determines that the brainwave is the Beta (β) wave. Furthermore, when the signal strength is estimated to be 90, the signal strength of Beta (β) wave is determined to be strong strength. Similarly, the processor 113 analyzes one or more brainwave-genres of the brainwave data, and estimates the signal strength of each brainwave-genre.

In some embodiments, after obtaining the brainwave data, the processor 113 transmits, through the transmission interface 117, the brainwave signal to the server 510 instead of analyzing the brainwave data. The server 510 processes the brainwave data to obtain the genre of the brainwave data and the signal strength of each genre of the brainwave data. The data processing ability of the server 510 is better than that of a general consumer device (such as the virtual reality device 110 in some embodiments). Therefore, in some embodiments, the processor 113 of the virtual reality device 110 only collects the brainwave data instead of processing the brainwave data, and the brainwave data which has not been analyzed is provided to the server 510 for further being processed and analyzed. Furthermore, the server 510 executes different procedures to obtain more precise emotion data of the user who is watching video, and to build the relationship between the classification of the video genre and the classification of the emotion data, in order that a much more stable video genre for the user can be recommended to the user who is watching video.

In some embodiments, the processor 113 analyzes the brainwave data to obtain one or more brainwave genres and the signal strength of each brainwave genre, and generates emotion data according to the brainwave genres and the signal strength of each brainwave genre. For example, Gamma (γ) wave of the brainwave data represents feeling of happiness of the user. When the signal strength of the Gamma (γ) wave is medium, it represents that the feeling of happiness of the user is medium level. For another example, Beta (β) wave represents feeling of excitement of the user. When the signal strength of the Beta (β) wave is strong, it represents that the user has more reaction to or is more excited at the video when the user watches it. That is to say, the current video is more likely to attract the user's attention or to make emotional reaction for the user. The emotion data can be, but is not limited to, the feeling of happiness, excitements, relaxation, concentration, tiredness, thinking, elation, and so on. It should be noted that the emotion data related to the brainwave data is not limited to one emotional state. The user may feel excited and tired at the same time when he/she is watching video, and the emotion data is excitement and tiredness.

The virtual reality device 110 transmits, through the transmission interface 117, the emotion data to the server 510. The server 510 generates a recommending list according to the received emotion data. The server 510 includes a video database which has a plurality of video, and each video is provided with at least one video genre. For example, when the video is a love comedy, the video genre includes the feeling of happiness and relaxation. When the video is horror, the video genres are excitement and elation, and so on. In some embodiments, when each video includes a plurality of video genres, each video genre is provided with a weighting factor. For example, when the video genres are happiness and excitement, the weighting factor of the happiness video genre could be 10, and the weighting factor of the excitement video genre could be 6, and so on. The weighting factor of each video genre is related to the content of the video and could be pre-determined by the processor 113 or the server 510.

The recommending list includes a plurality of video lists, and each video list has a video genre. Each video list includes a plurality of video links. The videos corresponding to the video links are the videos which have the same video genre. For example, the recommending list includes a first video lists (e.g., the video genre is happiness) and a second video lists (e.g., the video genre is excitement). The first recommending list includes the video link of the video having the happiness video genre. The second recommending list includes the video link of the video having the excitement video genre. Therefore, the server 510 searches, according to the emotion data, the video having the video genre related to the emotion data from video database. Then the server 510 generates or records the recommending list comprising a plurality of video lists, and each video list comprising the corresponding the video links. In some embodiments, the server 510 or the processor 113 determines whether to record the video links in the video list or not according to the weighting factor of the video genre. For example, when the emotion data is happiness and the emotion reaction is strong, the server 510 finds the weighting factor of the video genre related to the happiness are more than 8 and records those video links to the video lists. Therefore, the videos which are recommended for the user is more satisfied with the user's emotion strength.

The server 510 transmits the recommending list to the virtual reality device 110. The display 115 of the virtual reality device 110 shows a screen which includes the recommending list for the user to choose. In some embodiments, after the video links are chosen and clicked by the user, the virtual reality device 110 receives, through the transmission interface 117, a video stream from the server 510 and displaying the video. The screen includes the recommending list can be, but is not limited to, a pull-down menu, a table list, a nested list, and so on.

It should be noted that the user can log in to the server 510 through the internet when he/she operates the virtual reality device 110. For example, the server 510 is configured with a user-account database. The user-account database records the user's account, password, personal data (such as age, gender, favorite video type, history clicked-link data), the recommending list, and so on, and the data recorded in the user-account database is not limited herein. The recommending list which is generated according to the emotion data could be different from the user's account. Therefore, the video can be recommended to a specific user based on different user's preference and the brainwave, and the recommended video will be more adaptive for the specific user.

In some embodiments, when the user makes use of a function of watching video for the first time and there is no history data or record in the user-account database, the server 510 will predict at least one video genre that the user may like according to the user's age, gender, and some other personal data which are obtained at the user's registration, in order to generate a default video list. The default video list includes a plurality of video lists. Each video list includes its corresponding video genre. Each video list includes a plurality of video links of videos to be displayed on the virtual reality device 110.

Figure 2:
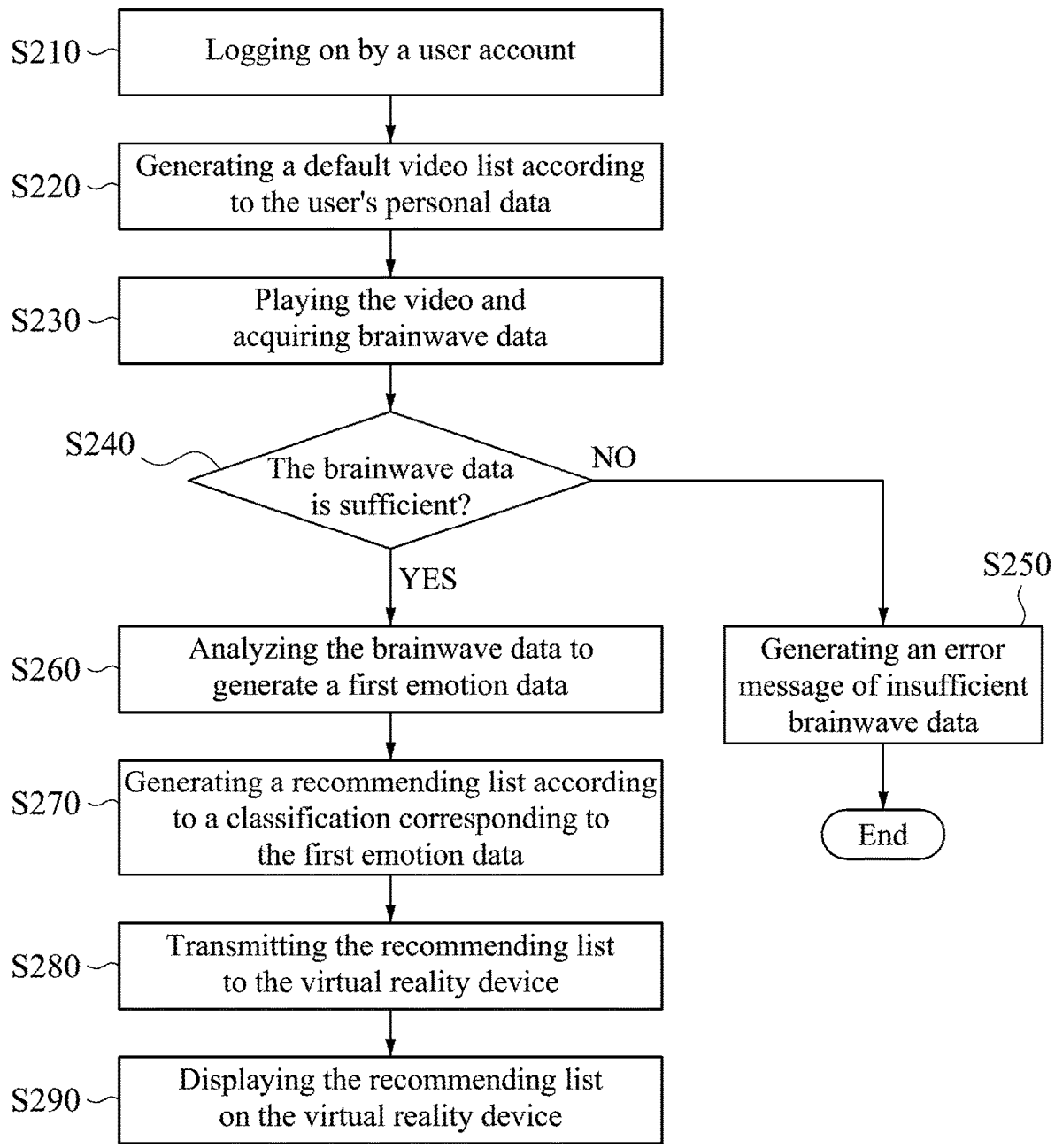
FIG. 2 is a flow chart illustrating a video recommending method in accordance with some aspects of the present disclosure.

Reference is made to FIG. 2, which is a flow chart illustrating a video recommending method in accordance with some aspects of the present disclosure. In some embodiments, the video recommending method of FIG. 2 is taken as an example that the server 510 has no user's history watching data. Incorporated with FIG. 1 and FIG. 2. In step S210, the user wears the virtual reality device 110, and operates the virtual reality device 110 via the screen on the display 115. The virtual reality device 110 transmits, through the transmission interface 117, the operations to the server 510 for registering and logging in to the server 510. In step S220, the server 510 generates the default video list according to the user's personal data and transmits the default video list to the virtual reality device 110.

In step S230, the default video list is displayed on the virtual reality device 110 for the user to click. In some embodiments, when the user clicks the video list which is "happiness" in the default video list, and the plurality of video links which relate to the video list of "happiness" are displayed. The user clicks one of the video links for playing the video. When the video is playing, the brainwave sensor 111 acquires the brainwave data which represents the user's current reaction or emotion for watching the video.

In step S240, after the video had been played to the end, a determination of whether the collected brainwave data is valid is made. In some embodiments, a run time of the video is determined whether is shorter than a threshold in order to determine whether the brainwave data is sufficient. For example, if the run time of the video is only one minute, the collected brainwave data is not valid or sufficient for recommending a video. A person of ordinary skill in the art can design other determinations for evaluating whether the brainwave data is sufficient, and the foresaid description is provided as an embodiment. In step S250, when the brainwave data is determined not to be valid, an error message is generated and transmitted to the server 510.

In step S260, when the brainwave data is valid or sufficient related to the video, the brainwave data is analyzed to generate a first emotion data. It should be noted that it can be the virtual reality device 110 or the server 510 which analyzes the brainwave data. The entity which analyzes the brainwave data is not limited. The description of the brainwave data which is analyzed for generating the first emotion data is described above and not repeated herein. In some embodiments, the virtual reality device 110 executes the procedure of analyzing the brainwave data, and then the virtual reality device 110 transmits the first emotion data to the server 510. In step S270, the server 510 generates the recommending list according to the classification corresponding to the first emotion data. In step S280, the server 510 transmits the recommending list to the virtual reality device 110. In step S290, the recommending list is displayed on the virtual reality device 110 for the user to click the video links, such that the user watches the videos.

Figure 3:
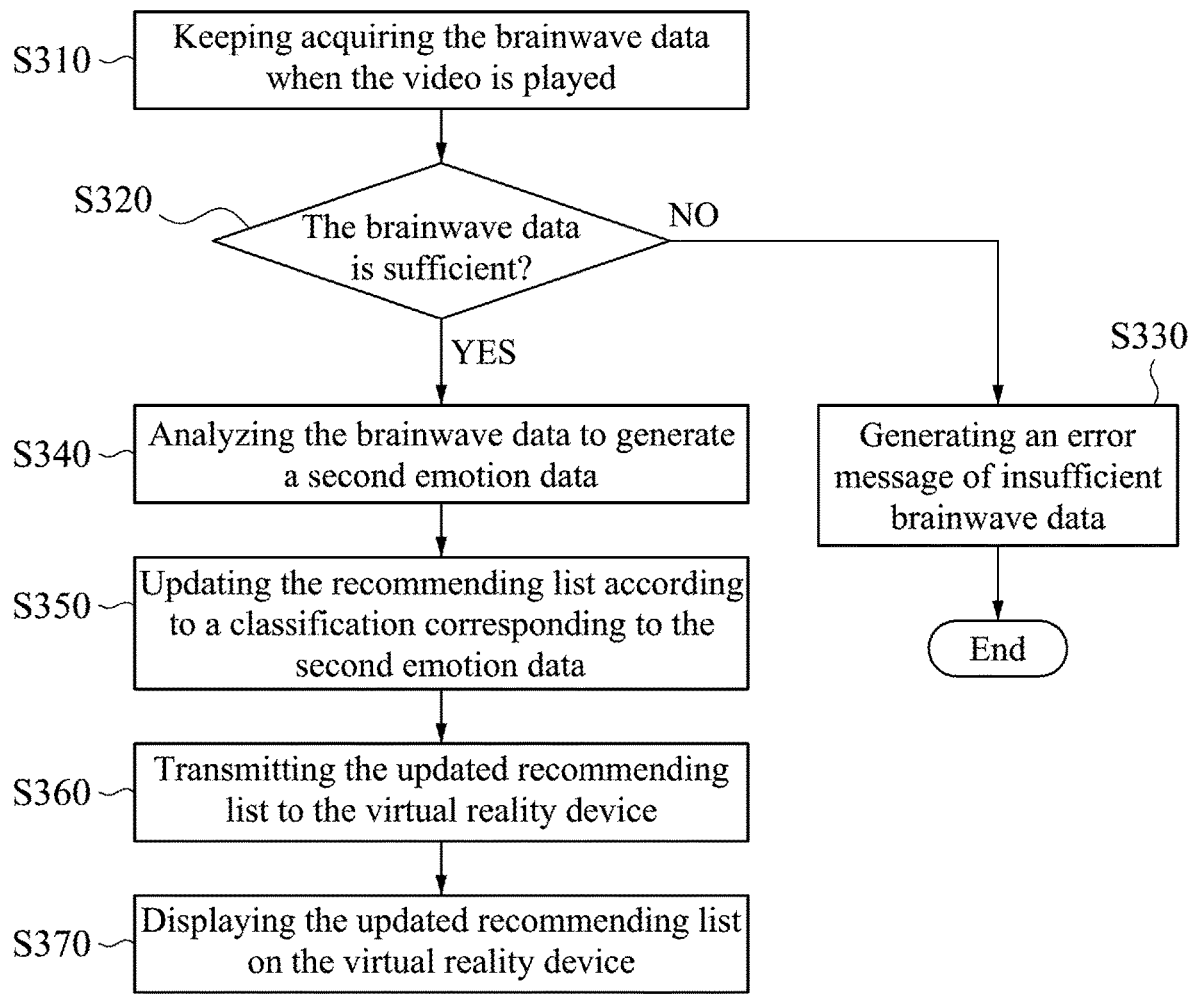
FIG. 3 is a flow chart illustrating a video recommending method in accordance with some other aspects of the present disclosure.

Reference is made to FIG. 3, which is a flow chart illustrating a video recommending method in accordance with some other aspects of the present disclosure. In some embodiments, the video recommending method of FIG. 3 illustrates that the server 510 has the user's history watching data, and further illustrates that the recommending list can be updated by the user's state. Incorporated with FIG. 1 and FIG. 3, in step S310, when the virtual reality device 110 plays the video, the brainwave sensor 111 keeps acquiring the brainwave data. In step S320, after the video had been played, the collected brainwave data is determined whether is sufficient. If the brainwave data is not sufficient, in step S330, the error message which the brainwave data is insufficient is generated and transmitted to the server 510.

If the brainwave data is sufficient, in step S340, the brainwave data which has been acquired is analyzed to generate a second emotion data. The illustration of generating the second emotion data is similar with the illustration of generating the first emotion data and not repeated herein. The virtual reality device 110 transmits the second emotion data to the server 510.

In step S350, the server 510 updates the recommending list according to the classification corresponding to the second emotion data. In some embodiments, the server 510 inspects whether the second emotion data corresponds to the video genre of the current-played video. For example, if the video genre of the current-played video is "happiness", however the inspected second emotion data is "excitement", it represents that the user watches the video which is tagged with "happiness", but actually the user's emotional reaction is excited. At this time, the second emotion data is determined not to match with the video genre. Then, the server 510 updates the plurality of video lists of the recommending list according to the second emotion data (such as "excitement").

The server 510 records the updated recommending list for the user's next playing. In step S360, if the user desires to watch the next video, the server 510 transmits the updated recommending list to the virtual reality device 110. In step S370, the updated recommending list is displayed on the virtual reality device 110. In some embodiments, if the user continues to watch the video and after step S370 of the video recommending method finished, back to step S310 for continuing detecting the user's emotion while he/she watches the video, in order to update the recommending list for the user.

As described above, the video recommending system and the video recommending method of the present disclosure can detect the brainwave data of the user to analyze the user's emotion while he/she is watching video. Because the default classification of the videos does not match the user's actual emotion while the user is watching the video at that time, the present disclosure provides the method to record data in order to update and recommend the video which is more close to the user's current emotion. Therefore, the problem that the default video classification does not correspond to the user's actual emotion is solved. The video which is playing corresponds to the user's current emotion state, and the user's trust and satisfaction in watching video is improved. Furthermore, the virtual reality device 110 (such as a head-mounted virtual reality helmet) in the present disclosure is used for the user to watch video. Because the brainwave signal can be acquired when the VR helmet is worn at the user's head, the discomfort can be reduced when the brainwave is acquired, such that there is no discomfort or strange feeling for the user while the videos recommending procedure is executing.

It is to be understood that the specific order or hierarchy of steps in the methods disclosed is an illustration of exemplary processes. Based upon design preferences, it is understood that the specific order or hierarchy of steps in the methods may be rearranged. The accompanying method claims present elements of the various steps in a sample order, and are not meant to be limited to the specific order or hierarchy presented unless specifically recited therein.

The novel algorithms described herein may also be efficiently implemented in software and/or embedded in hardware.

It will be apparent to those skilled in the art that various modifications and variations can be made to the structure of the present disclosure without departing from the scope or spirit of the disclosure. In view of the foregoing, it is intended that the present disclosure cover modifications and variations of this disclosure provided they fall within the scope of the following claims.

What is claimed is:

1. A video recommending system, comprising:
a virtual reality device, comprising:
a brainwave sensor configured to acquire a first brainwave data; and
a processor coupled to the brainwave sensor, and configured to receive the first brainwave data; and
a server coupled to the virtual reality device, wherein the server comprises a video database which stores a plurality of videos and each video corresponds to at least one video genre, and each of the video genres corresponds to a weighting factor;
wherein the server is configured to retrieve a first emotion data and a second emotion data from the first brainwave data, and search a first video genre according to the first emotion data and select the videos of the first video genre by a first weighting factor regarding strength of the first emotion and search a second video genre according to the second emotion data and select the videos of the second video genre by a second weighting factor regarding strength of the second emotion to generate a recommending list;
wherein the server is configured to transmit the recommending list to the virtual reality device, wherein the recommending list comprises a plurality of video lists for the virtual reality device to play at least one video of the video lists.

2. The video recommending system of claim 1, wherein the virtual reality device further comprises a display coupled to the processor, wherein when the display plays the at least one video, the brainwave sensor acquires a second brainwave data, and the server determines, according to a third emotion data corresponding to the second brainwave data, whether the third emotion data corresponds to a video genre of the at least one video being played currently.

3. The video recommending system of claim 2, wherein the processor generates, according to the first brainwave data and the second brainwave data, the first emotion data, the second emotion data, and the third emotion data respectively, or the server generates, according to the first brainwave data and the second brainwave data, the first emotion data, the second emotion data, and the third emotion data respectively.

4. The video recommending system of claim 2, wherein when the first emotion data and/or the second emotion data is determined not corresponds to the video genre of the at least one video being played, the server updates the video lists of the recommending list according to the third emotion data.

5. The video recommending system of claim 1, wherein when the at least one video is played, the processor is further configured to determine whether a run time of the at least one video is shorter than a threshold, and when the run time is shorter than the threshold, the processor generates an error message.

6. A video recommending method, comprising:
acquiring a first brainwave data, wherein a video database stores a plurality of videos and each video corresponds to at least one video genre, and each of the video genres corresponds to a weighting factor;
analyzing the first brainwave data to generate a first emotion data and a second emotion data;
searching a first video genre according to the first emotion data and selecting the videos of the first video genre by a first weighting factor regarding strength of the first emotion, and searching a second video genre according to the second emotion data and selecting the videos of the second video genre by a second weighting factor regarding strength of the second emotion to generate a recommending list;
transmitting the recommending list to a virtual reality device, wherein the recommending list comprises a plurality of video lists; and
playing, by the virtual reality device, at least one video of the video lists.

7. The video recommending method of claim 6, further comprising:
acquiring a second brainwave data in response to playing the at least one video; and
analyzing the second brainwave data to generate a third emotion data.

8. The video recommending method of claim 7, further comprising:
determining, by a server, whether the third emotion data corresponds to a video genre of the at least one video being played currently.

9. The video recommending method of claim 8, further comprising:
updating the video lists of the recommending list according to the third emotion data when the first emotion data and/or the second emotion data is determined not corresponds to the video genre of the at least one video being played.

10. The video recommending method of claim 6, further comprising:
determining whether a run time of the at least one video is shorter than a threshold; and
generating an error message when the run time is shorter than the threshold.

* * * * *